United States Patent [19]
Evans et al.

[11] Patent Number: 5,540,658
[45] Date of Patent: Jul. 30, 1996

[54] TRANSCERVICAL UTERINE ACCESS AND SEALING DEVICE

[75] Inventors: Michael A. Evans, Palo Alto; William R. Dubrul, Redwood City; Hen Lao, Santa Clara, all of Calif.

[73] Assignee: Innerdyne, Inc., Sunnyvale, Calif.

[21] Appl. No.: 266,036

[22] Filed: Jun. 27, 1994

[51] Int. Cl.$^6$ .................................................. A61M 29/00
[52] U.S. Cl. ............................ 604/101; 604/55; 604/271
[58] Field of Search ............................ 604/49, 54, 55, 604/96, 101, 104–107, 271

[56] References Cited

U.S. PATENT DOCUMENTS

| | | | |
|---|---|---|---|
| 3,312,215 | 4/1967 | Silber | 604/104 X |
| 4,430,076 | 2/1984 | Harris . | |
| 4,503,843 | 3/1985 | Boebel . | |
| 4,641,634 | 2/1987 | Storz . | |
| 4,664,114 | 5/1987 | Ghodsian | 604/101 X |
| 4,779,612 | 10/1988 | Kishi . | |
| 4,820,270 | 4/1989 | Hardcastle | 604/96 |
| 4,836,189 | 6/1989 | Allred, III et al. . | |
| 4,885,003 | 12/1989 | Hillstead | 604/22 |
| 4,911,148 | 3/1990 | Sosnowski et al. . | |
| 4,949,718 | 8/1990 | Neuwirth et al. . | |
| 5,041,093 | 8/1991 | Chu | 604/104 |
| 5,104,377 | 4/1992 | Levine | 604/101 |
| 5,122,122 | 6/1992 | Allgood | 604/174 |
| 5,242,390 | 9/1993 | Goldrath . | |
| 5,259,836 | 11/1993 | Thurmond et al. . | |

OTHER PUBLICATIONS

ZSI, Zinnanti Surgical Instruments, Inc. Product Literature/brochure.
Bard® Cervical Cannula, Product Literature/brochure, ©1993.
Storz, Uterine Cannulas and Elevators, Product Literature/brochure.

*Primary Examiner*—Corrine M. McDermott
*Attorney, Agent, or Firm*—Townsend and Townsend and Crew LLP

[57] ABSTRACT

A cervical access device includes a tubular body having a proximal end, a distal end, and a lumen extending therebetween. A first expansible occlusion member is disposed near the distal end of the tubular body, and a second occlusion member is proximally spaced apart from the first occlusion member. Together, the first and second occlusion members define a reduced diameter neck for receiving the cervical os. In an exemplary aspect, the first occlusion member includes an evertible cylindrical surface which assumes a conical configuration which diverges in the distal direction when actually compressed. The second occlusion member can also be provided with a conical configuration which diverges in the proximal direction so that the first and second occlusion members when brought together define a neck having opposed tapered walls. A catheter for providing thermal treatment to the uterus can be introduced through the cervical access device to perform thermal treatment on the uterus. The cervical access device provides a seal with the cervical os to help prevent heated thermally conductive medium introduced by the catheter from leaking around the cervical access device outwardly into the vagina.

33 Claims, 10 Drawing Sheets

TRANSCERVICAL UTERINE ACCESS AND SEALING DEVICE

BACKGROUND OF THE INVENTION

1. Field of the Invention

The present invention relates generally to methods and apparatus for introducing medical instruments into the uterus. In particular, the present invention relates to a transcervical uterine access device which provides thermally insulated access to the uterus through the cervix and which substantially inhibits thermally conductive media from exiting the uterus around the access device and into the vagina.

"Minimally invasive" surgical procedures have recently been developed as alternatives to conventional "open" surgery. Of particular interest to the present invention, are minimally invasive surgical procedures relating to treatment of the uterus. More particularly, of interest to the present invention are least invasive and other surgical techniques which rely on a catheter to deliver heat to the interior of the uterus. As described in detail in U.S. Pat. No. 5,045,056 and co-pending application Ser. No. 08/266,037 (attorney docket no. 13178-8-2), the disclosures of which are incorporated herein by reference, the inner lining of the uterus, known as the endometrium, can be thermally destroyed by heating the endometrium to a temperature sufficient to effectuate necrosis. To heat the endometrium, a thermally conductive medium can be introduced into the uterus and maintained at a temperature sufficient to induce necrosis. The medium can be delivered to the uterus by a catheter which is inserted through the cervix and which is provided with a heating element to heat the medium within the uterus.

Such thermal treatment procedures can be problematic in certain respects. For instance, a cannula or sheath is typically inserted through the vagina and the cervix to provide an access channel or lumen into the uterus. It is difficult to provide a seal between the cervix and the cannula to prevent the medium from leaking around the cannula and outwardly toward the vagina. Leakage of hot medium past the cannula presents the possible risk of injury to the vagina and cervix.

A further problem can arise when heat from the catheter or the heated fluid is transferred through the cannula and to the vagina or the cervix. This heat transfer also presents the possible risk of injury to the vagina and cervix.

Another problem can arise when inserting the catheter through the cannula. The cannula may not be sufficiently anchored to the cervical os permitting the cannula to move within the cervix. Such movement is undesirable since it increases the potential for leakage.

For these and other reasons, it would be desirable to provide improved methods and apparatus for the introduction of a thermally conductive medium into the uterus to provide thermal treatment to the uterus. It would be particularly desirable to provide a transcervical uterine access device that could both provide access to the uterus for a catheter delivering the medium and substantially inhibit undesired release of the medium from the uterus.

2. Description of the Background Art.

Hysteroscopes providing visual access and working channels through the endocervical canal into the uterus are described in U.S. Pat. Nos. 4,911,148; 4,836,189; 4,779,612; 4,641,634; and 4,503,843. A cannula for introducing heated fluids and having an insulative sheath which engages the outer cervix is described in U.S. Pat. No. 5,242,390. An inflatable bladder for distending and heating the uterus is described in U.S. Pat. No. 4,949,718. A hysterography device having a cup at a distal end for seating on the cervix is described in U.S. Pat. No. 5,259,836.

SUMMARY OF THE INVENTION

The present invention provides methods and apparatus for affording thermally insulated access to the uterus through the cervix. The apparatus includes a transcervical uterine access device for placement through the vagina and the endocervical canal and into the uterus. The transcervical uterine access device includes a tubular body having a proximal end, a distal end, and a lumen extending therebetween. The lumen provides a path through which a catheter (or other medical instrument) can be introduced into the uterus through the vagina.

The transcervical uterine access device further includes a first expansible occlusion member disposed near the distal end of the tubular body. The first occlusion member assists in substantially inhibiting leakage of a thermally conductive medium from the uterus, around the access device, and into the vagina. A second occlusion member proximally spaced apart from the first occlusion member is also provided. The two occlusion members define a reduced diameter neck therebetween for receiving the cervical os and anchoring the access device in the cervical os.

The second occlusion member is preferably axially translatable relative to the first occlusion member, permitting adjustment of the length of the reduced diameter neck.

In a preferred aspect, the first occlusion member is expansible from a collapsed configuration which closely conforms to the exterior surface of the tubular body to a conical configuration which diverges in the distal direction. The second occlusion member can also be provided with a conical configuration which diverges in the proximal direction so that the first and second occlusion members when brought together define a neck having opposed tapered walls.

In an exemplary aspect, the first occlusion member comprises an evertible cylindrical surface which assumes a conical configuration which diverges in the distal direction when axially compressed. In a preferred aspect, the evertible surface includes an elastomeric sheet covering a mesh. In still another aspect, the transcervical uterine access device includes a tubular shaft having a proximal end, a distal end, and a lumen extending therebetween. The tubular shaft is slidably disposed within the lumen of the tubular body with the distal end of the tubular shaft being attached to the distal end of the evertible cylindrical surface. Distal translation of the body relative to the shaft axially compresses and radially expands the evertible cylindrical surface.

In a further exemplary aspect, the tubular body of the transcervical uterine access device has a length in the range from 15 cm to 30 cm, and an outside diameter in the range from 5 mm to 10 mm. In still a further aspect, the transcervical uterine access device includes a hemostasis valve on the tubular body at the proximal end of the lumen.

In a method according to the present invention, access to a patient's uterus is provided through a tubular body having an access lumen. Preferably, the tubular body will be insulated. According to the method, the tubular body is introduced through the cervical os into the uterus. A first occlusion member is then expanded over an exterior surface of the tubular body and positioned against an internal surface of the internal cervical os. A sufficient sealing force is provided to form a seal between the first occlusion member and the inner surface of the cervical os to substantially inhibit loss of pressurized fluid from the uterus into the vagina.

In one particular aspect of the method, the first occlusion member is in a collapsed configuration which closely conforms to the exterior surface when the tubular body is introduced through the endocervical canal. The first occlusion member is expanded to a conical configuration having a surface that engages the internal surface of the cervical os. In a preferred aspect, the first occlusion member includes an evertible cylindrical surface which is expanded by axially compressing the cylindrical surface to cause the distal end to expand radially. In another preferred aspect, the evertible cylindrical surface includes an elastomeric sheet covering a mesh.

In a further aspect of the method, a second occlusion member on the tubular body is engaged against the external os of the cervix to enhance anchoring and sealing. The second occlusion member will usually have a conical surface which is engaged against the external os of the cervix by axially translating the second occlusion member over the tubular body.

DETAILED DESCRIPTION OF THE SPECIFIC EMBODIMENTS

The present invention provides methods and apparatus for affording access to the uterus through the cervix. The apparatus includes a transcervical uterine access device for placement through the vagina and the endocervical canal into the uterus. The transcervical uterine access device includes a tubular body having a proximal end, a distal end, and a lumen extending therebetween. The lumen provides a path through which a catheter (or other medical instruments) can be introduced into the uterus through the vagina. The tubular body will have a length which is sufficient to allow the access lumen to extend through the endocervical canal and into the uterus. Preferably, the length of the tubular body will be in the range from about 15 cm to 30 cm. In a preferable aspect, the tubular body is insulated to substantially inhibit heat transfer through the tubular body and to the cervix, vagina or surrounding tissues. Preferably, the tubular body will have an extruded insulative layer. The insulative layer is provided with voids to inhibit the heat transfer.

In an exemplary aspect, the lumen provides a path for a thermal treatment catheter which delivers and heats a thermally conductive medium to the uterus to provide thermal treatment of the uterus. To assist in substantially inhibiting leakage of the thermally conductive medium from the uterus, around the access device, and into the vagina, the transcervical uterine access device further includes a first expansible occlusion member disposed near the distal end of the tubular body. When the first expansible occlusion member is expanded and seated against the inner os of the cervix, a seal is provided which inhibits leakage of the medium around the access device. The access device will usually also include a second occlusion member proximally spaced apart from the first occlusion member. The two occlusion members together define a reduced diameter neck for receiving the internal and external cervical os and to assist in anchoring the access device in the cervix.

The first occlusion member is expansible so that the tubular body can be inserted through the cervical os and into the uterus before the first occlusion member is expanded. When the tubular body is advanced through the cervix, the first occlusion member will substantially conform to the outside geometry of the tubular body to reduce profile and facilitate advancement. After the first occlusion member is within the uterus, it can be expanded and positioned proximally against the internal os of the cervix. When positioned against the internal os with a sufficient force, a seal is provided which substantially inhibits fluid within the uterus from leaking through the cervical canal past the access device.

The second occlusion member is axially translatable relative to the first occlusion member. After the first occlusion member is placed in the uterus, the second occlusion member can be advanced towards the first occlusion member until the second occlusion member is positioned against the external os of the cervix. The second occlusion member will preferably be seated against the external os with sufficient compression to provide a second seal to assist in substantially inhibiting fluid within the uterus from leaking past the endocervical canal through which the neck of the access device extends. The length of the neck can be changed by axially translating the second occlusion member relative to the first occlusion member, typically over a distance in the range from 0 cm to 10 cm, allowing adjustment according to the particular length of the cervical canal.

Together, the occlusion members provide an anchor for the access device within the cervical canal. Such anchoring substantially inhibits the access device from sliding within the cervix when a catheter is inserted or withdrawn from the access lumen. In an exemplary aspect, the occlusion members (when expanded) will radially extend from the tubular body to a diameter in the range from about 10 mm to 25 mm, preferably from about 10 mm to 15 mm. This amount of radial extension will be sufficient to provide the necessary seal and to anchor the access device at the internal cervical os.

A variety of medical instruments can be introduced through the lumen of the access device including diagnostic hysteroscopes. Of particular interest is a thermal treatment catheter which disposes a thermally conductive medium into the uterus. The catheter can be provided with a heating element to heat the medium in the uterus. Alternatively, the catheter can inject a preheated fluid into the uterus. To prevent the medium in the uterus from escaping through the lumen and out of the patient, a hemostasis valve can be provided on the tubular body at the proximal end of the lumen. The hemostasis valve in connection with the seal formed by the occlusion members allows the uterus to substantially maintain the fluid within the uterus to effectuate necrosis of the endometrial lining. Such devices are described in U.S. Pat. No. 5,045,056 and copending application Ser. No. 08/266,037 (attorney docket no. 13178-8-2) the full disclosures of which are incorporated herein by reference.

In another aspect of the access device, the tubular body is attached to a handle assembly. The handle assembly provides a convenient grip for positioning the tubular body. The handle assembly can also be used to expand the first occlusion member as described hereinafter. In an exemplary aspect, the tubular body can be detachable from the handle assembly so that the handle assembly can be reusable after the tubular body is disposed.

Figures 1, 2B:
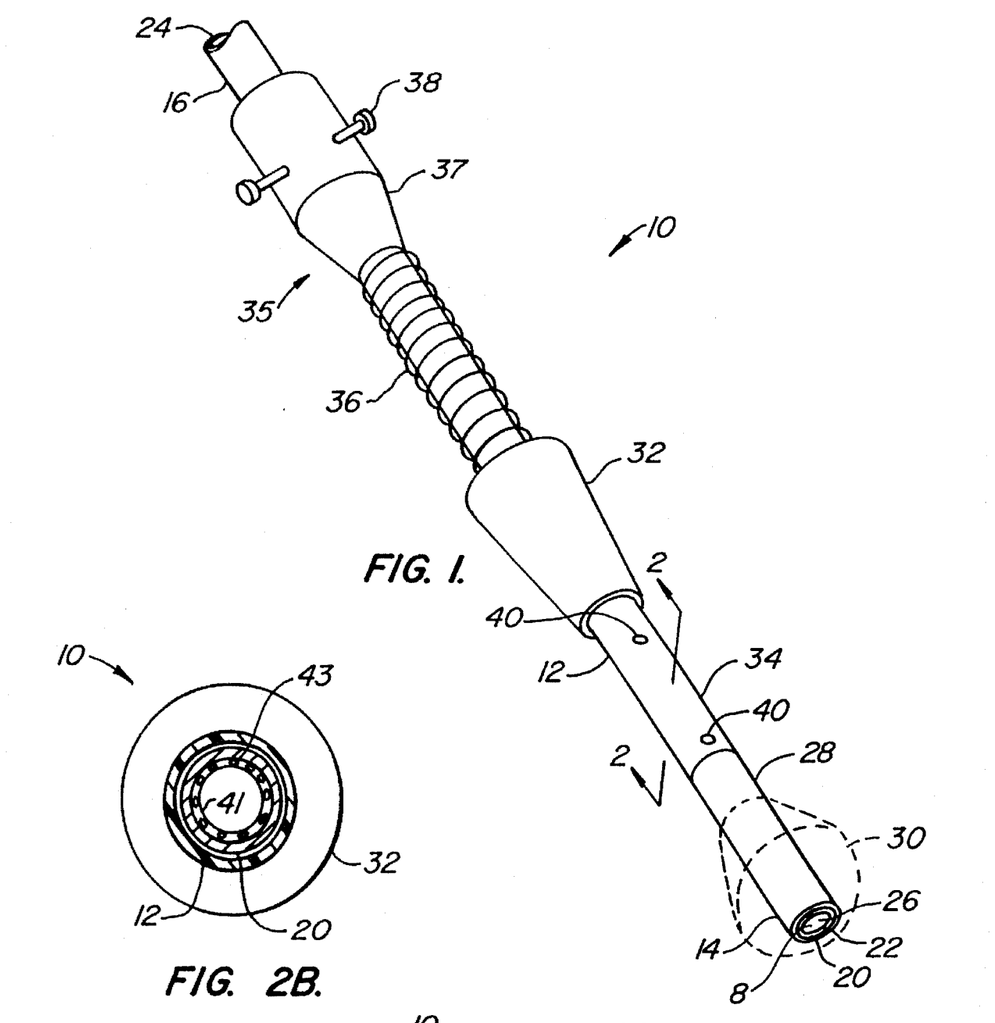
FIG. 1 is a perspective view illustrating a distal portion of a transcervical uterine access device according to the present invention.
FIG. 2B is the cross-sectional view of FIG. 2A showing the addition of an insulative layer.
Figure 2A:
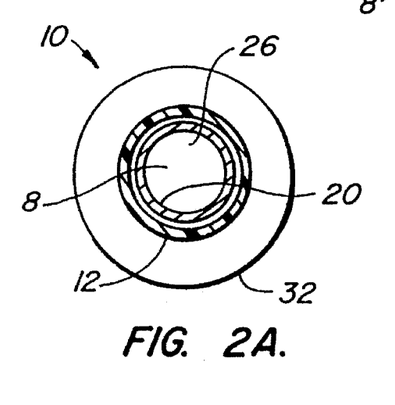
FIG. 2A is a cross-sectional view taken along line 2—2 of FIG. 1.

An exemplary embodiment of a distal portion of a transcervical uterine access device 10 is shown in FIGS. 1 and 2A. The access device 10 includes a tubular body 12 having a distal end 14 and a proximal end 16. An access lumen 18 extends between the distal end 14 and the proximal end 16. Slidably disposed within the access lumen 18 of the tubular body 12 is a tubular shaft 20. The tubular shaft 20 has a distal end 22 and a proximal end 24, and a lumen 26 extending between the distal end 22 and the proximal end 24. The distal end 22 of the tubular shaft 20 is attached to the distal end 14 of the tubular body 12. As will be described in detail hereinafter, distal translation of the tubular body 12 relative to the tubular shaft 20 will axially compress and radially expand an evertible cylindrical surface 28 on the tubular body 12 to form a first expansible occlusion member 30 (shown in dotted line) near the distal end 14 of the tubular body 12.

The access device 10 further includes a second occlusion member 32 that is proximally spaced apart from the first occlusion member 30. The first and second occlusion members 30 and 32 together define a reduced diameter neck 34 for receiving the internal and external cervical os. In an exemplary aspect, the second occlusion member 32 is axially translatable relative to the first occlusion member 30 to allow the length of the neck 34 to be adjustable.

Proximal to the second occlusion member 32 is an external sealing sub-assembly 35 for securing the second occlusion member 32 against the external os of the cervix. The sub-assembly 35 includes a compressible spring 36 and a locking member 37. As the locking member 37 is advanced towards the second occlusion member 32, the spring 36 compresses and biases the second occlusion member 32 against the external os of the cervix. Once the locking member 37 is advanced sufficiently to provide the necessary sealing force to the second occlusion member 32, a compression pin 38 on the locking member 37 is depressed to secure the locking member 37 to the tubular body 12. As an alternative to the sub-assembly 35, a variety of mechanisms can be used to secure the second occlusion member 32 to the tubular body when the second occlusion member 32 is position against the external os including, latches, clamps, bolts, o-rings, and the like.

Optionally, the transcervical uterine access device 10 can further include temperature sensing elements 40 on the exterior surface of the access device 10. The temperature sensing elements 40 are placed over regions where leakage from the cervix or heat transfer might be expected. The temperature sensing elements 40 are used to insure that heated fluid from the cervix is not leaking peripherally over the access device 10. Means for monitoring the temperatures of these elements (not illustrated) is provided. If an unexpected temperature rise is detected by the temperature sensing elements 40, heated fluid can rapidly be withdrawn from the uterus and treatment stopped until a better seal is achieved.

As shown in FIG. 2B, transcervical uterine access device 10 can optionally be provided with an insulative layer 41. The insulative layer 41 can be constructed of any insulative material that can assist in substantially inhibiting heat from transferring through the walls of the access lumen 18. In an exemplary aspect, the insulative layer 41 can be constructed of an extruded polymer material having voids 43. Alternatively, insulative layer 41 can be constructed of an open cell foam; a preferable material being urethane. Optionally, the tubular shaft 20 can be constructed of a thermally insulative material.

Figure 3:
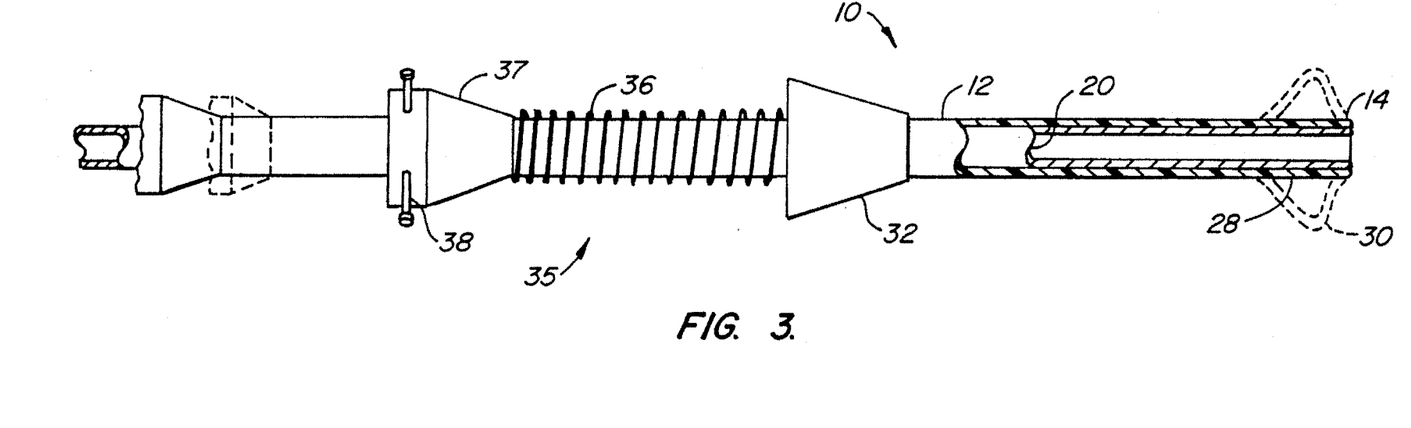
FIG. 3 is a distal cutaway side view of the access device of FIG. 1.
Figure 4:
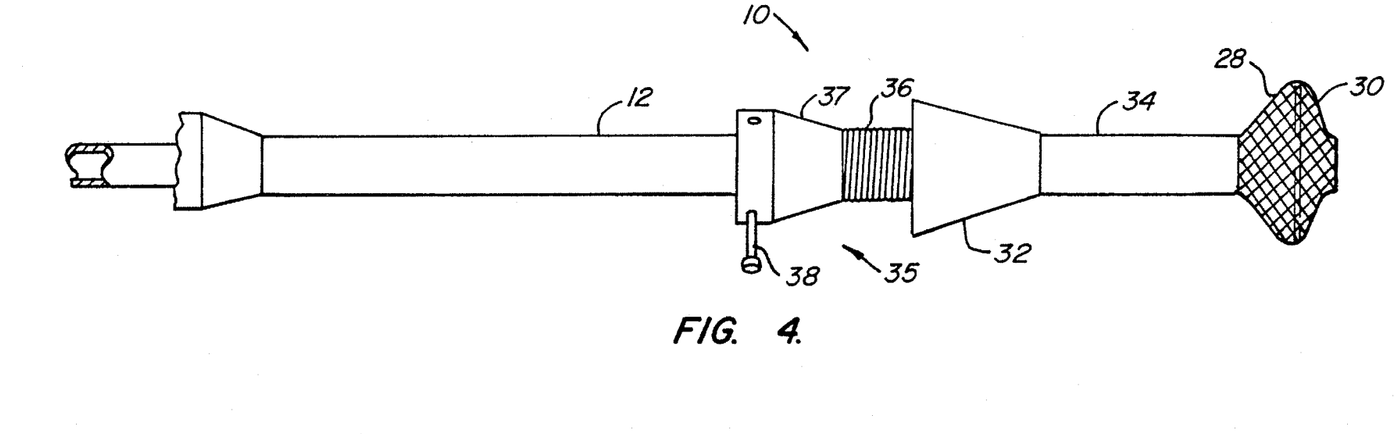
FIG. 4 is a side view of the access device of FIG. 3 showing a first occlusion member in an expanded configuration and having the second occlusion member in close proximity to the first occlusion member to define a neck having opposed tapered walls.

Referring to FIGS. 3–4, the construction and operation of the access device 10 will be described in greater detail. As previously described, the distal ends of both the tubular body 12 and the tubular shaft 20 are connected. Distal translation of the tubular body 12 relative to the tubular shaft 20 causes the evertible cylindrical surface 28 to both axially compress and radially expand (as shown in FIG. 4) to form the first occlusion member 30. Alternatively, the tubular shaft 20 can be axially translated in a proximal direction relative to the tubular body 12 to cause compression and expansion of the evertible cylindrical surface 28.

The evertible cylindrical surface 28 is preferably constructed from an elastomeric sheet covering a mesh or braided material. Exemplary materials for the mesh or braided material include polymer strands such as PET, polypropylene, polyethylene, and the like. Exemplary materials for the elastomeric sheet include latex, silicone, thermoplastic elastomers (such as C-Flex, commercially available from Consolidated Polymer Technology), and the like. The mesh is formed into a cylindrical geometry and is translatably disposed over the tubular shaft 20. The distal ends of both the mesh and sheet are attached to the distal end of the tubular shaft 20 so that when the evertible cylindrical surface 28 is axially compressed, the evertible cylindrical surface 28 will both axially compress and radially expand to form the first occlusion member 30. To insure that the evertible cylindrical surface 28 will radially expand to the desired configuration, the mesh can be pre-fatigued, heat forged or bonded in preselected locations, e.g., along a circumferential line. When the mesh is axially compressed, the mesh will radially expand about the line as shown in FIG. 4.

In an exemplary aspect, the mesh can also be used to form the tubular body 12 by proximally extending the mesh from the evertible cylindrical surface 28. A cover tube can be placed over the extended mesh so that the exterior surface of the tubular body 12 is substantially flush with the evertible cylindrical surface 28. An exemplary material for constructing the cover tube is a cross linked heat shrink polymer. In this manner, the evertible cylindrical surface 28 can be made to closely conform to the exterior of the tubular body 12.

The tubular shaft 20 can be constructed from a variety of materials including stainless steel, composite filament wound polymer, or extruded polymer tubing (such as Nylon 11 or Ultem, commercially available from General Electric), and the like. These materials have sufficient strength so that the tubular body 20 will not collapse when inserted into the cervix or when the evertible cylindrical surface 28 is compressed.

When forming the first occlusion member 30, the evertible cylindrical surface 28 preferably assumes a conical configuration which diverges in the distal direction. Preferably, the outer diameter of the first occlusion member 30 will be in the range from about 1.0 cm to 2.5 cm. The second occlusion member 32 will also preferably have a conical configuration which diverges in the proximal direction so that the first and second occlusion 30 and 32 when brought together define the neck 34 having opposed tapered walls. Preferably, the outer diameter of the second occlusion member will be in the range from about 1.0 cm to 2.5 cm.

As shown in FIG. 4, once the first occlusion member 30 is formed by axially translating the tubular body 12, the second occlusion member 32 can be axially advanced toward the first occlusion member 30. The axial advancement of the second occlusion member 32 reduces the length of the neck 34 so that the access device 10 can be adjusted to the size of the cervical os. Once in the desired position, the second occlusion member 32 can be held against the external os of the cervix by advancing the sealing subassembly 35 and by depressing the pin 38 to secure the locking member 37 to the tubular body 12.

Figure 5:
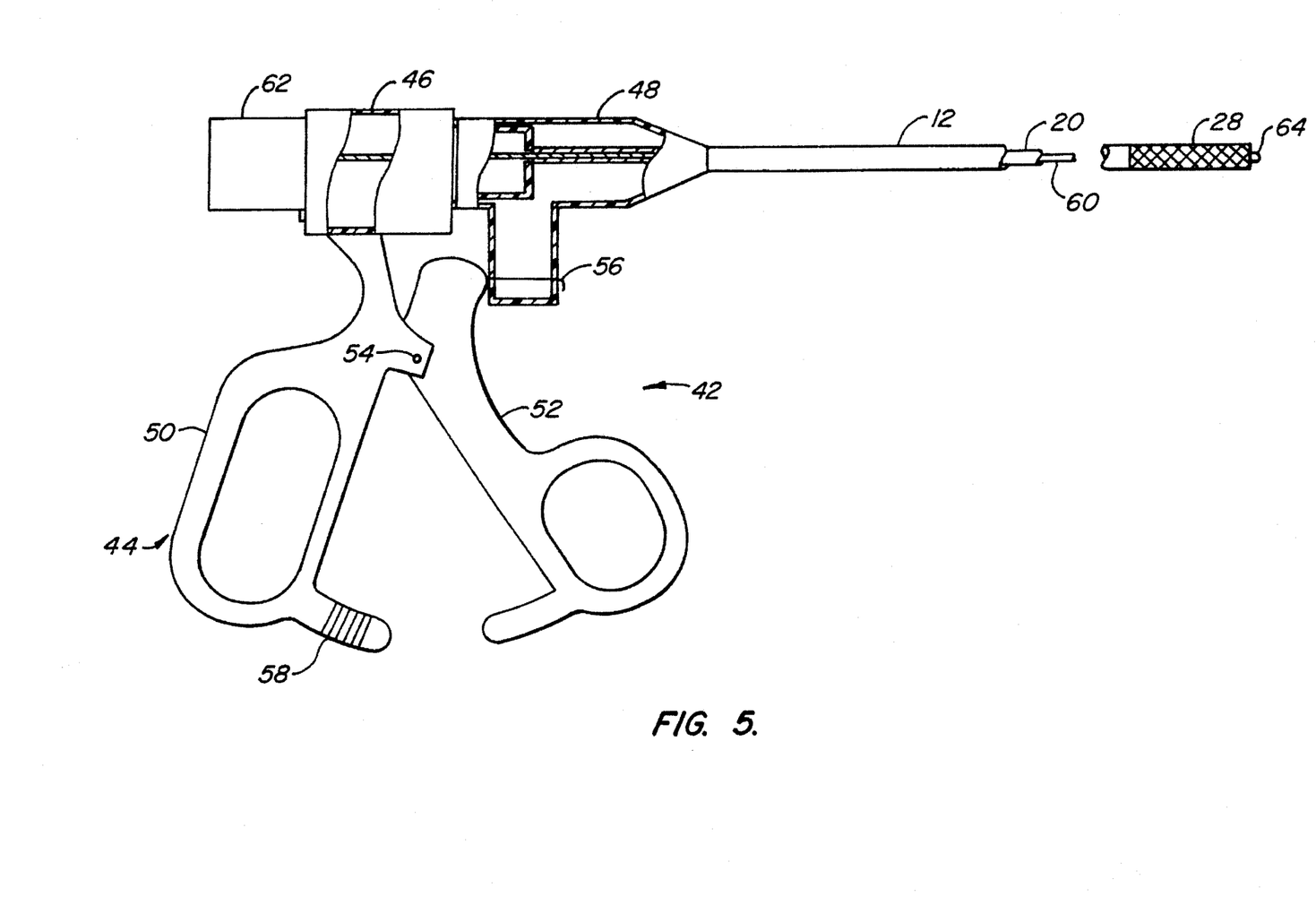
FIG. 5 is a side view of an exemplary embodiment of a transcervical uterine access device according to the present invention.
Figure 6:
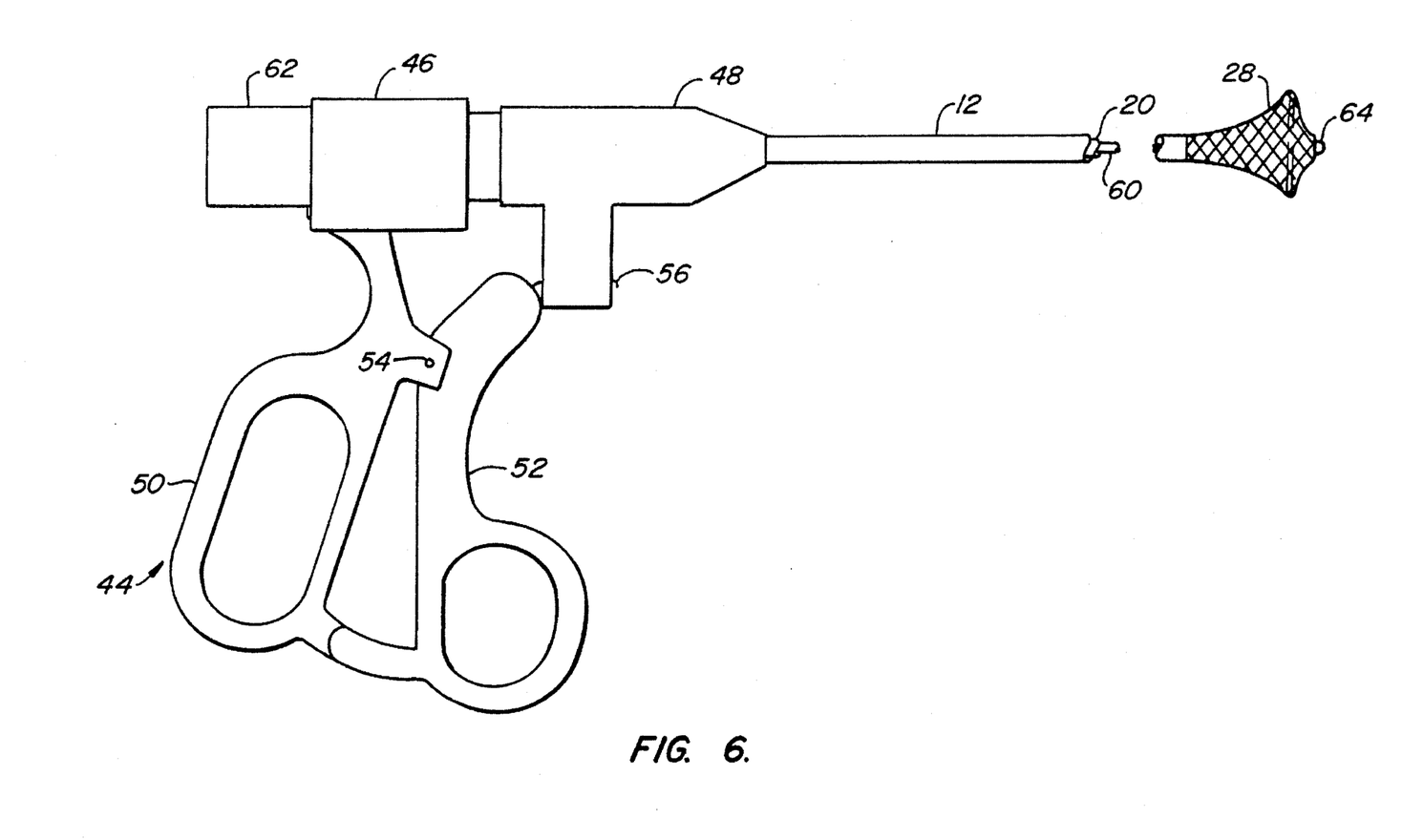
FIG. 6 is a side view of the access device of FIG. 5 showing the first occlusion member in an expanded configuration.

To axially translate the tubular body 12 relative to the tubular shaft 20, a variety of mechanisms can be employed; a primary feature being that the tubular body 12 is axially translated relative to the tubular body 20 to effectuate axial compression of the evertible cylindrical surface 28. A convenient way to axially compress the evertible cylindrical surface 28 is to prevent axial movement of the tubular shaft 20 while axially advancing the tubular body 12 in the distal direction. An exemplary mechanism for distally translating the tubular body 12 relative to the tubular shaft 20 is a handle assembly 42 as shown in FIGS. 5–6.

The handle assembly 42 includes a scissor type handle 44, a base member 46, and a translatable member 48. The components of the handle assembly 42 can be constructed of any rigid material including stainless steel, reinforced polymer material, and the like. The handle 44 includes a first lever 50 and a second lever 52. The two levers 50 and 52 are pivotally joined by a pivot pin 54. The first lever 50 is attached to the base member 46 which is in turn attached to the tubular shaft 20. The second lever 52 is positioned against the translatable member 48 by a wire 56. When the levers 50 and 52 are advanced towards each other, the second lever 52 causes the translatable member 48 to axially advance in the distal direction as shown in FIG. 6. The translatable member 48 is attached to the tubular body 12 so that axial translation of the translatable member 48 causes the tubular body 12 to axially advance over the tubular shaft 20. This causes the evertible cylindrical surface 28 to both axially compress and radially expand as previously described. Optionally, the two levers 50 and 52 can have serrations 58 which interlock when the members are brought together and maintain the evertible cylindrical surface 28 at a desired diameter. Also, markers can be placed on the handle 44 near the serrations 58 to indicate the degree of radial expansion of the evertible cylindrical surface 28 as the two levers 50 and 52 are brought together.

To assist in insertion of the access device 10 into the uterus, a positioning shaft 60 can be inserted through the lumen 26 of the tubular shaft 20. The positioning shaft 62 has an attachment member 62 for attachment to the base member 46, and an atraumatic end 64 which is sounded against the fundus of the uterus during insertion. This assists in the proper placement of the access device 10 within the uterus.

Figure 7:
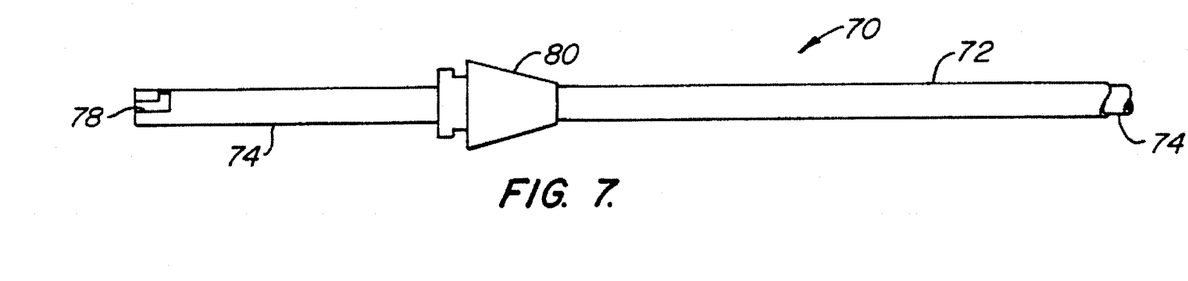
FIG. 7 is a side view of a detachable anchor portion of a transcervical uterine access device according to the present invention.
Figure 8:
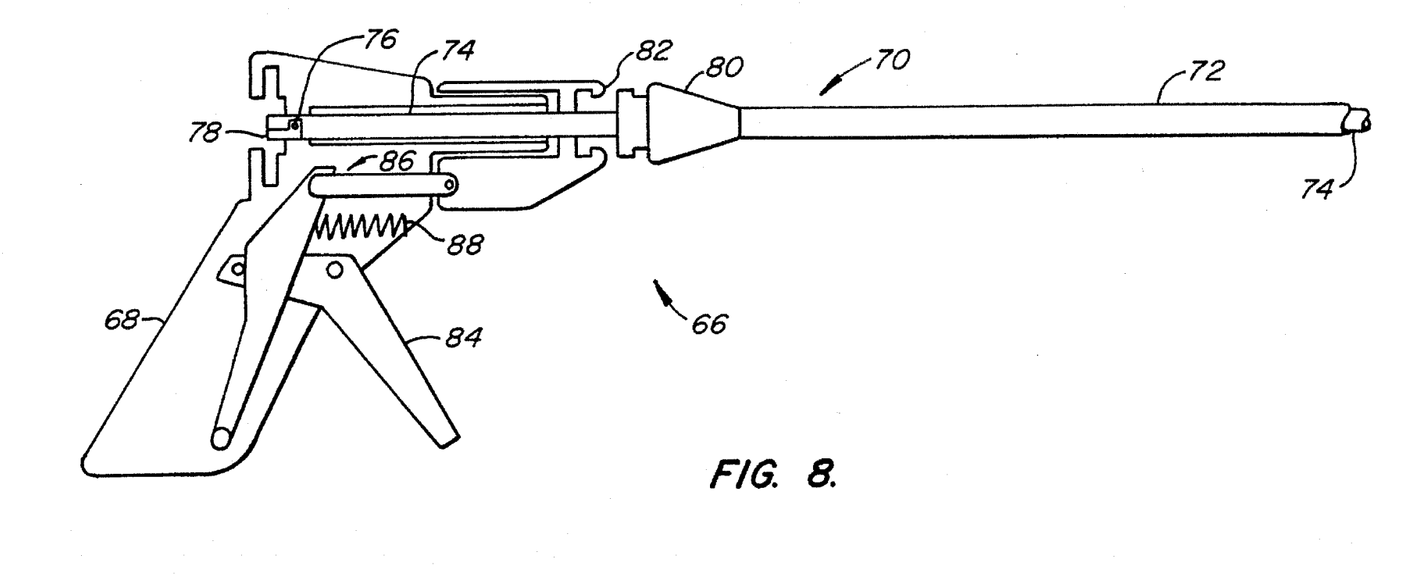
FIG. 8 is a side view of an access device showing the detachable anchor portion of FIG. 7 inserted into a reusable handle assembly according to the present invention.

In one particular aspect of the invention, the handle assembly 44 can be detachable from the tubular body 12 and the tubular shaft 20 so that the handle assembly 44 can be reused. By having a reusable handle, costs incurred when treating the uterus can be reduced. A further exemplary embodiment of an access device 66 having a reusable handle assembly 68 is shown in FIGS. 7 and 8.

The access device 66 includes an anchor portion 70 that is removable from the handle assembly 68. The anchor portion 70 includes a tubular body 72 over a tubular shaft 74 and operates essentially identical to the body 12 and shaft 20 previously described in FIG. 1 to radially expand an evertible cylindrical surface (not shown). The tubular shaft 74 is secured to the handle assembly 68, preferably by a pin 76 inserted into a slot 78 of the tubular shaft 74. Connected to the tubular body 72 is a transition portion 80 which is removably received into a pair of jaws 82 of the handle assembly 68. Convenient removal of the anchor portion 70 from the handle assembly 68 is accomplished by removing the transition portion 80 from the jaws 82 and by turning the shaft 74 and sliding it from the pin 76.

To axially advance the tubular body 72 over the tubular shaft 74, a trigger 84 is depressed which axially advances the jaws 82 by a linking mechanism 86. This in turn advances the tubular body 72 while the tubular shaft 74 is prevented from axially translating by the handle assembly 68. Axial translation of the tubular body 72 relative to the tubular shaft 74 forms a first occlusion member as previously described. Optionally, a spring 88 can be provided to assist in returning the trigger 84 to its starting position when removing the access device 66 from the uterus. After removal from the uterus, the anchor portion 70 can be removed from the handle assembly 68 and discarded.

Figures 9, 12:
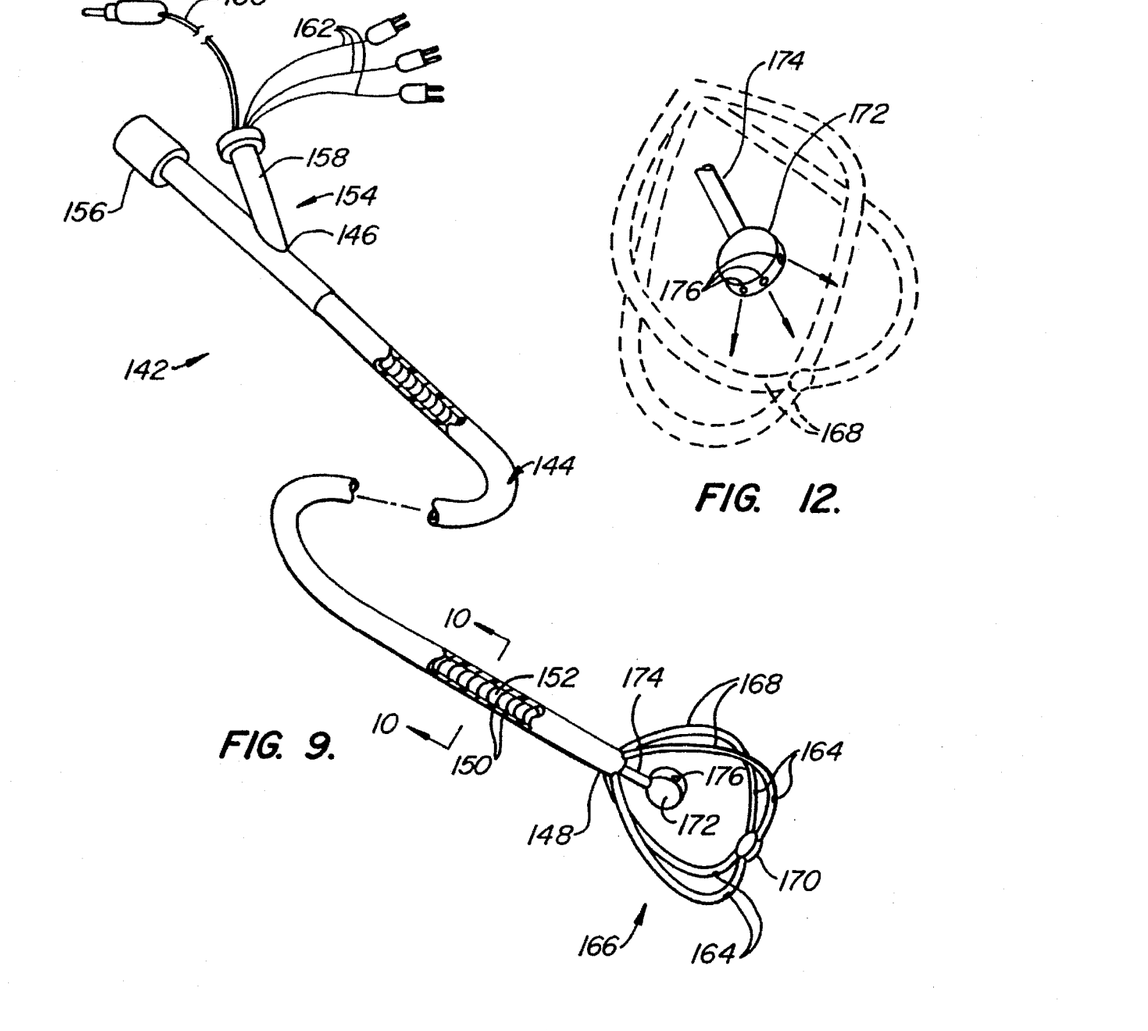
FIG. 9 is a perspective view of a thermal treatment catheter having a heating element distributed over a central lumen of the catheter and which can be inserted into the access device of FIG. 1.
FIG. 12 is a detailed view of a flow distribution element located at the distal end of the catheter of FIG. 9, shown with an expandable cage structure in broken line.
Figures 10, 11:
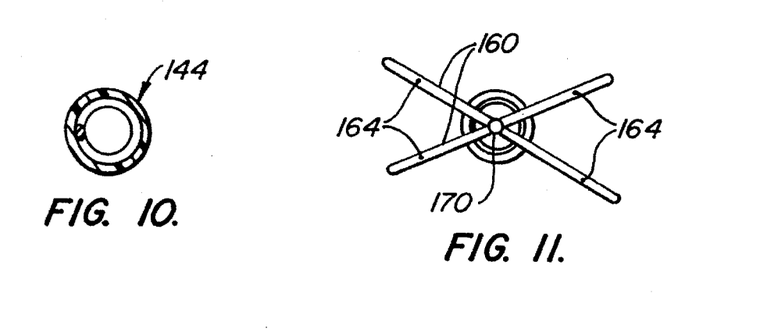
FIG. 10 is a cross-sectional view taken along line 10—10 of FIG. 9.
FIG. 11 is an end view of the catheter of FIG. 9.

Referring to FIGS. 9–12, an exemplary embodiment of a thermal treatment catheter 142 for use with the transcervical uterine access device 10 is shown. Construction and use of the catheter 142 is described in detail in co-pending application Ser. No. 08/226,037 (Attorney Docket No. 13178-8-2), filed on the same date as the present application. Briefly, the catheter 142 includes an elongate element or body 144 having a proximal end 146 and a distal end 148. The catheter body 144 is tubular having a wire coil heating element 150 formed over an axial lumen 152 thereof. A proximal housing 154, typically in the form of a conventional Y-connector, includes a proximal port 156 for connection to a source for providing a thermally conductive fluid, such as a combined power supply, pressure monitor and oscillatory pump. Typically, a conventional compression fitting will be provided on the port 156 to allow connection via tubing. A second port 158 on the housing 154 provides for a power connector 160, which is connected to the wire coil heating element 150, and a plurality of temperature sensing leads 162, typically being thermocouple connectors. The leads 162 will be connected to a thermocouple 164 located on a cage structure 166, attached to the distal end 148 of the elongate catheter body 144. The cage structure 166 comprises four resilient elements or "ribs" 168 which are secured at a proximal end of the distal end of the catheter body 144 and to each other by means of a distal button 170. As will be described in more detail hereinafter, the cage structure 166 will be introduced to the uterus in a collapsed configuration within the access device 10, and will thereafter expand to the open configuration, as illustrated in FIGS. 9, 11, and 12.

A flow distributing element 172 is connected via a short tube 174 to the distal end of lumen 152 through catheter body 144. The flow distributing element 172 includes a plurality of flow ports 176 which are oriented to distribute flow in a preselected pattern. As best seen in FIG. 12, three flow ports 176 may be provided to direct flow in three diverging directions within a single plane, such a configuration is particularly useful for treatment of the uterus, where the outermost ports are generally directed at the cornua regions of the uterus which might otherwise receive insufficient heating from catheter 142.

Figure 13:
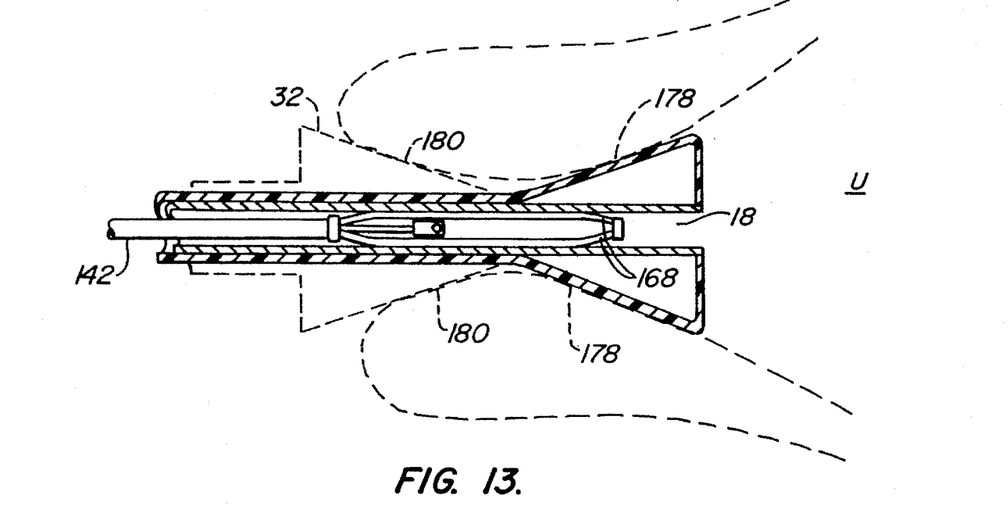
FIGS. 13–14 illustrate the placement of the access device of FIG. 1 and the catheter of FIG. 9 in the uterus.
Figure 14:
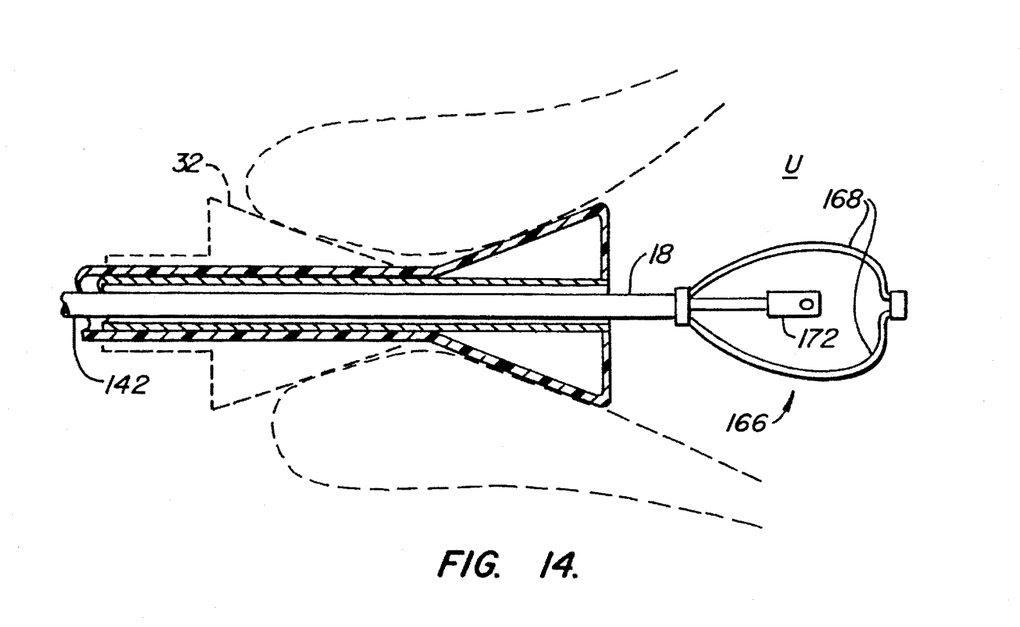

Placement of the transcervical uterine access device 10 within the cervical canal, and the introduction of the catheter 142 into the uterus U is shown in FIGS. 13 and 14. The first occlusion member 30 is positioned against the internal os 178 of the uterus. The conical configuration of the first occlusion member 30 provides for a general adherence to the internal os 178 to form a seal. The seal helps to prevent pressurized fluid within the uterus from exiting the uterus through the interface between the internal os 178 and the first occlusion member 30. The second occlusion member 32 (shown in dotted line) is positioned against the external os 180 of the uterus and forms a second seal similar to the seal formed by the first occlusion member 30. In addition to providing a seal, the first and second occlusion members 30 and 32 also anchor the access device 10 within the cervical canal.

With the access device 10 being secured within the cervical canal, the catheter 142 can be advanced through the access lumen 18 and into the uterus U. The ribs 168 of the catheter 142 are collapsible (as shown in FIG. 9) so that the catheter 142 can be advanced through the access lumen 18. When the cage structure 166 is within the uterus, the ribs 168 can be expanded as shown in FIG. 10. The catheter 142 is now ready to distribute fluid into the uterus through the flow distribution element 172.

Figure 15:
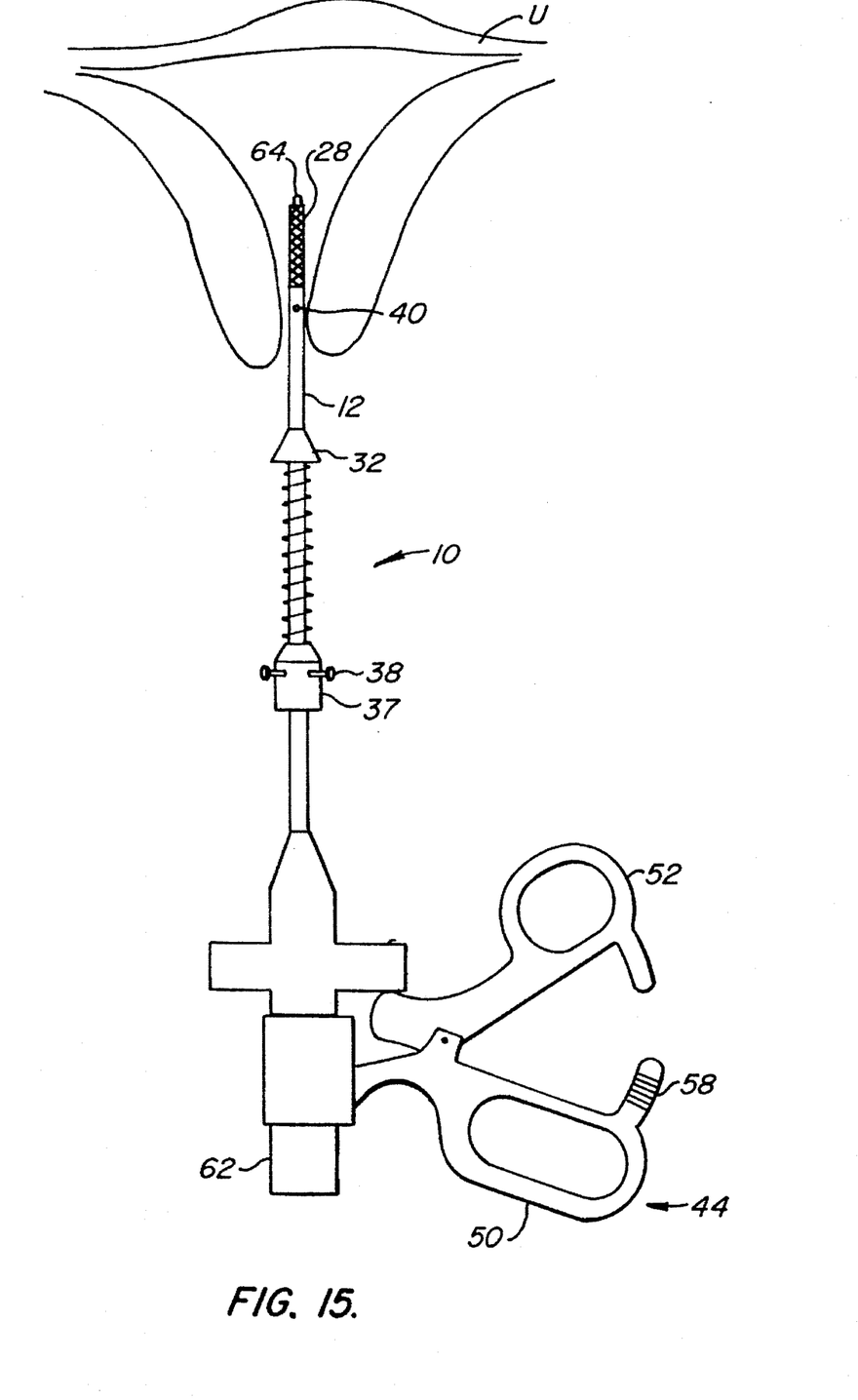
FIGS. 15–17 illustrate use of the access device of FIG. 1 in combination with the catheter of FIG. 9 in thermally treating the uterus according to the present invention.
Figure 16:
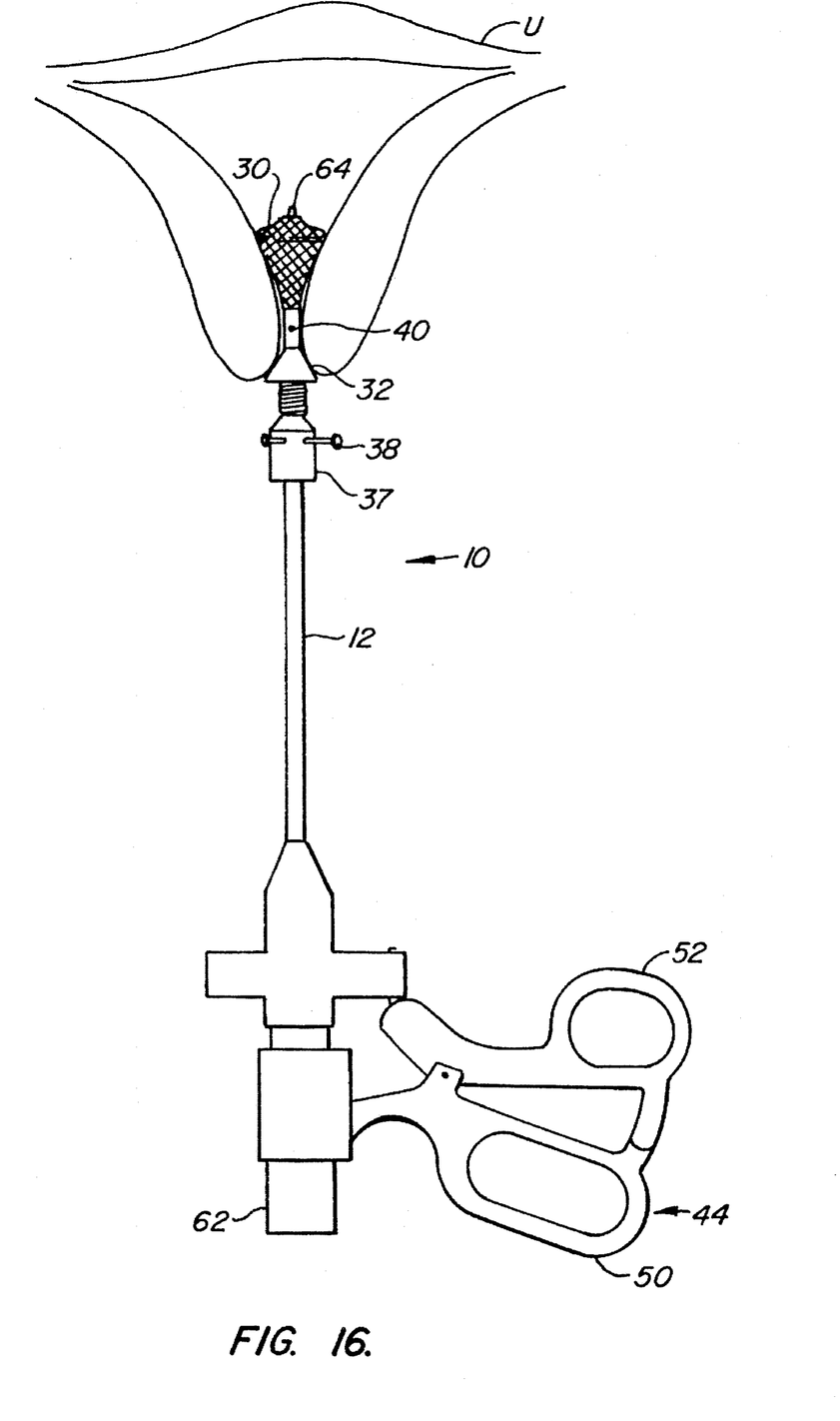

Referring now to FIGS. 15–17, use of the catheter 142 and transcervical uterine access device 10 in thermal treatment of the uterus U will be described. Access to the cervical canal is first obtained in a conventional manner. After access is obtained, the transcervical uterine access device 10 is introduced through the vagina and cervix while the evertible cylindrical surface 28 is in a collapsed configuration, as shown in FIG. 15. When the atraumatic end 64 is sounded against the fundus of the uterus, distal advancement of the access device 10 is ceased. The evertible cylindrical surface 28 is then expanded by placing a thumb in the first lever 50 and a finger in the second lever 52 of the handle 44. The two members 50 and 52 are then squeezed together to axially advance the tubular body 12 over the tubular shaft 20 to form the first occlusion member 30, as illustrated in FIG. 16. The serrations 58 can then be engaged to maintain the shape of the first occlusion member 30. The access device 10 is then drawn proximally outward until the first occlusion member 30 engages the inner os of the cervix and a seal is formed. The second occlusion member 32 is then advanced distally by distal movement of the locking member 37 until the inner and outer surfaces of the cervix are engaged by the first occlusion member 30 and the second occlusion member 32, respectively. The compression pin 38 is then depressed to secure the locking member 37 to the tubular body 12 and to hold the second occlusion member 32 in place. In this configuration, the access device 10 provides a generally fluid tight seal about its periphery so that thermally conducted medium which is introduced as described hereinafter cannot leak around the device 10 outwardly into the vagina. If the access device 10 is provided with an insulative material (as shown in FIG. 2B), the access device 10 can also be used to substantially inhibit heat transfer to the cervix, vagina and surrounding tissue which can occur when treating the uterus with the thermally conductive medium.

Figure 17:
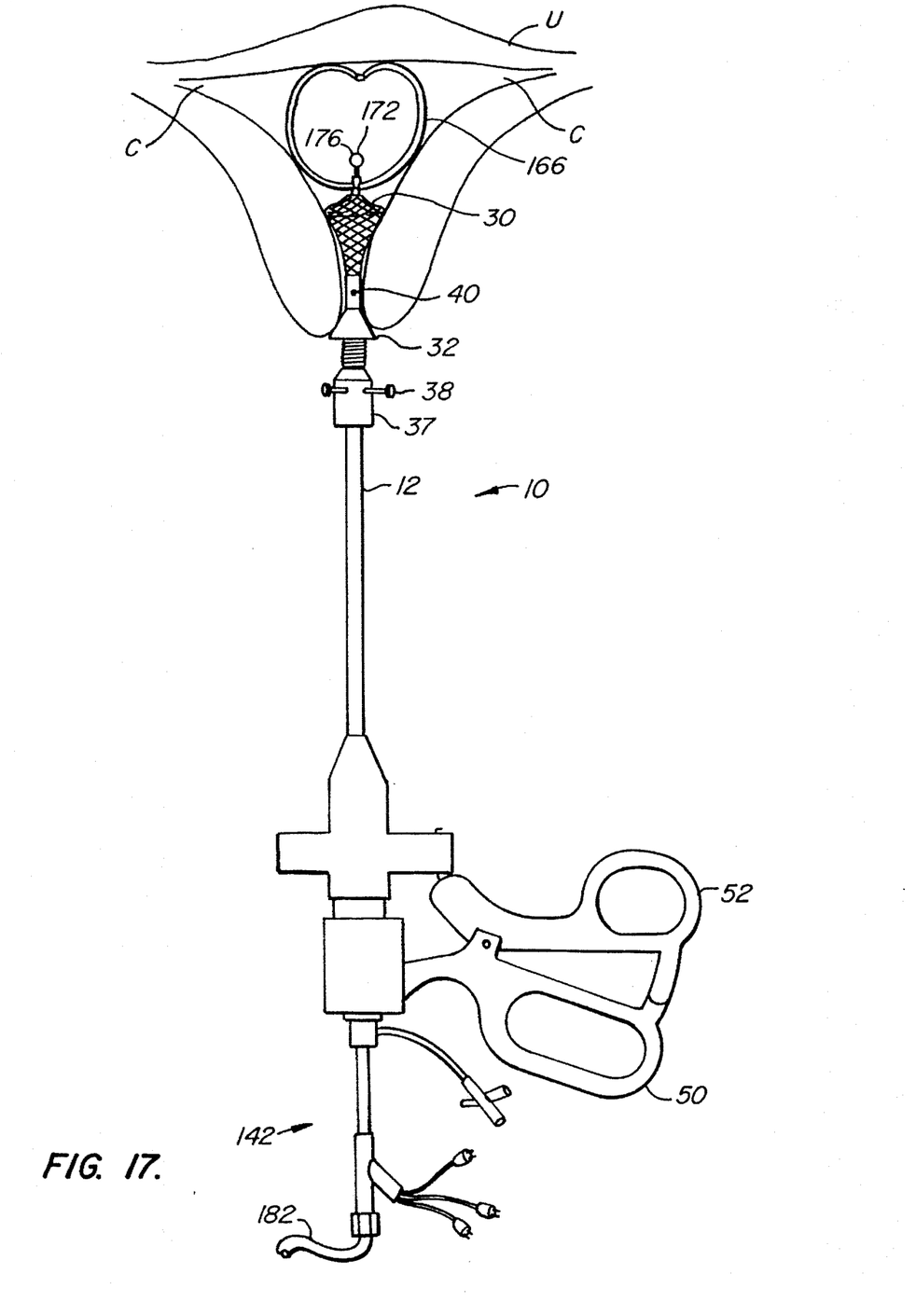

After the access device 10 is properly positioned, the positioning shaft 60 is removed from the access device by grasping the base member 62 and sliding the shaft from the lumen 26. The thermal treatment catheter 142 is then introduced through the lumen 26. The catheter 142 will be introduced with the cage structure 166 being collapsed. When the cage structure 166 enters the uterus, it will expand into the interior of the uterus as shown in FIG. 17. The flow distributing element 172 will thus be located within the interior of the uterus so that fluid flow therefrom is directed toward the cornua regions C, in order to enhance thermal transfer to these regions. The center port 176 of the flow distributing element 172 will direct fluid centrally within the uterine cavity. In order to assure that heated fluid is not leaking peripherally over the access device 10 or that the temperature inside the cervix is not too high, the temperature sensing elements 40 can be provided on its exterior surface as previously described.

Heat treatment can be achieved by introducing a heated or unheated thermally conductive medium through the catheter 142 using the connector tube 182. The connector tube 182 will be connected to a suitable heating and oscillatory pumping system. The system will deliver electrical energy to internal heating coils 150 (shown in FIG. 9), while fluid is oscillated back and forth within the uterine cavity. The treatment will be continued for a time sufficient to induce necrosis of endometrial lining of the uterus. The access device 10 can be used to assist in preventing excessive heat from transferring from the catheter 142 and to the cervix, vagina, or other tissue.

Although the foregoing invention has been described in detail for purposes of clarity of understanding, it will be obvious that certain modifications may be practiced within the scope of the appended claims.

What is claimed is:

1. A transcervical uterine access device comprising:

a tubular body having a proximal end, a distal end, and a lumen extending therebetween;

a first expansible occlusion member disposed near the distal end of the tubular body;

a second occlusion member proximally spaced-apart from the first occlusion member and sized to be received in the vagina and against the external os of the cervix, the second occlusion member being axially translatable relative to the first occlusion member, wherein the first and second occlusion members define a reduced-diameter neck therebetween for receiving the cervical os; and wherein the first occlusion member is expansible from a collapsed configuration closely conforming to the exterior surface of the tubular body to a conical configuration which diverges in the distal direction, and wherein the second occlusion member has a conical configuration which diverges in the proximal direction so that the first and second occlusion members when brought together define a neck having opposed tapered walls.

2. A transcervical uterine access device as in claim 1, wherein the tubular body has a length in the range from 15 cm to 30 cm and an outside diameter in the range from 5 mm to 10 mm.

3. A transcervical uterine access device as in claim 1, wherein the first occlusion member comprises an evertible cylindrical surface connected to the distal end of the tubular body which assumes a conical configuration which diverges in the radial direction upon axial translation of the tubular body which axially compresses and radially expands the evertible cylindrical surface.

4. A transcervical uterine access device as in claim 3, further comprising a tubular shaft having a proximal end, a distal end, and a lumen extending therebetween, wherein the tubular shaft is slidably disposed within the lumen of the tubular body with the distal end of the tubular shaft attached to a distal end of the evertible cylindrical surface, wherein the distal end of the tubular body is attached to a proximal end of the evertible cylindrical surface, wherein distal translation of the body relative to the shaft will axially compress and radially expand the evertible cylindrical surface.

5. A transcervical uterine access device as in claim 4, wherein the tubular shaft is constructed of a thermally insulative material.

6. A transcervical uterine access device as in claim 4, further comprising an insulative material within the lumen of the tubular shaft.

7. A transcervical uterine access device as in claim 6, wherein the insulative material includes an extruded polymer having voids.

8. A transcervical uterine access device as in claim 6, wherein the insulative material is constructed of urethane.

9. A transcervical uterine access device as in claim 1, wherein the first occlusion member radially extends from the tubular body to a diameter in the range from about 10 mm to 25 mm.

10. A transcervical uterine access device as in claim 1, wherein the first occlusion member radially extends from the tubular body to a diameter in the range from about 10 mm to 15 mm.

11. A transcervical uterine access device comprising:

a tubular body having a proximal end, a distal end, and a lumen extending therebetween;

a first expansible occlusion member disposed near the distal end of the tubular body;

a second occlusion member proximally spaced-apart from the first occlusion member and sized to be received in the vagina and against the external os of the cervix, the second occlusion member being axially translatable relative to the first occlusion member, wherein the first and second occlusion members define a reduced-diameter neck therebetween for receiving the cervical os, wherein the first occlusion member comprises an evertible cylindrical surface connected to the distal end of the tubular body which assumes a conical configuration which diverges in the radial direction upon axial translation of the tubular body which axially compresses and radially expands the evertible cylindrical surface;

a tubular shaft having a proximal end, a distal end, and a lumen extending therebetween, wherein the tubular shaft is slidably disposed within the lumen of the tubular body with the distal end of the tubular shaft attached to a distal end of the evertible cylindrical surface, wherein the distal end of the tubular body is attached to a proximal end of the evertible cylindrical surface, wherein distal translation of the body relative to the shaft will axially compress and radially expand the evertible cylindrical surface; and an insulative material within the lumen of the tubular shaft.

12. A transcervical uterine access device as in claim 11, wherein the insulative material includes an extruded polymer having voids.

13. A transcervical uterine access device as in claim 11, wherein the insulative material is constructed of urethane.

14. A transcervical uterine access device as in claim 11, further comprising a handle assembly which is removable from the body and the shaft, and wherein the handle includes a first lever, means for coupling the first lever to the tubular shaft, a second lever, and means for coupling the second lever to the tubular body, wherein manual actuation of the levers expands the first occlusion member.

15. A transcervical uterine access device comprising:

a tubular body having a proximal end, a distal end, and a lumen extending therebetween;

a first expansible occlusion member disposed near the distal end of the tubular body;

a second occlusion member proximally spaced-apart from the first occlusion member and sized to be received in the vagina and against the external os of the cervix, the second occlusion member being axially translatable relative to the first occlusion member, wherein the first and second occlusion members define a reduced-diameter neck therebetween for receiving the cervical os; and wherein the first occlusion member comprises an evertible surface constructed of an elastomeric sheet covering a mesh.

16. A transcervical uterine access device as in claim 15, wherein the tubular body is insulated.

17. A transcervical uterine access device comprising:

a tubular body having a proximal end, a distal end, and a lumen extending therebetween;

a first expansible occlusion member disposed near the distal end of the tubular body;

a second occlusion member proximally spaced-apart from the first occlusion member and sized to be received in the vagina and against the external os of the cervix, the second occlusion member being axially translatable relative to the first occlusion member, wherein the first and second occlusion members define a reduced-diameter neck therebetween for receiving the cervical os, wherein the first occlusion member comprises an evertible cylindrical surface connected to the distal end of the tubular body which assumes a conical configuration which diverges in the radial direction upon axial translation of the tubular body which axially compresses and radially expands the evertible cylindrical surface;

a tubular shaft having a proximal end, a distal end, and a lumen extending therebetween, wherein the tubular shaft is slidably disposed within the lumen of the tubular body with the distal end of the tubular shaft attached to a distal end of the evertible cylindrical surface, wherein the distal end of the tubular body is attached to a proximal end of the evertible cylindrical surface, wherein distal translation of the body relative to the shaft will axially compress and radially expand the evertible cylindrical surface; and a handle assembly which is removable from the body and the shaft, and wherein the handle includes a first lever, means for coupling the first lever to the tubular shaft, a second lever, and means for coupling the second lever to the tubular body, wherein manual actuation of the levers expands the first occlusion member.

18. A transcervical uterine access device comprising:

an insulated tubular body having a proximal end, a distal end, and a lumen extending therebetween;

a first expansible occlusion member disposed near the distal end of the tubular body;

a second occlusion member proximally spaced-apart from the first occlusion member and sized to be received in the vagina and against the external os of the cervix, the second occlusion member being axially translatable relative to the first occlusion member, wherein the first and second occlusion members define a reduced-diameter neck therebetween for receiving the cervical os.

19. A transcervical uterine access device as in claim 18, wherein the first occlusion member is expansible from a collapsed configuration closely conforming to the exterior surface of the tubular body to a conical configuration which diverges in the distal direction.

20. A transcervical uterine access device as in claim 19, wherein the second occlusion member has a conical configuration which diverges in the proximal direction so that the first and second occlusion members when brought together define a neck having opposed tapered walls.

21. A transcervical uterine access device as in claim 18, wherein the first occlusion member comprises an evertible surface constructed of an elastomeric sheet covering a mesh.

22. A transcervical uterine access device comprising:

an insulated tubular body having a proximal end, a distal end, and a lumen extending therebetween;

a first expansible occlusion member disposed near the distal end of the tubular body; and a second occlusion member proximally spaced-apart from the first occlusion member, wherein the first and second occlusion members define a reduced-diameter neck therebetween for receiving the cervical os.

23. A transcervical uterine access device comprising:

a tubular body having a proximal end, a distal end, and a lumen extending therebetween;

a first expansible occlusion member disposed near the distal end of the tubular body;

a second occlusion member proximally spaced-apart from the first occlusion member and sized to be received in the vagina and against the external os of the cervix;

wherein the first and second occlusion members define a reduced-diameter neck therebetween for receiving the cervical os; and a sealing sub-assembly slidably held over the tubular body, the sealing sub-assembly comprising a locking member and a biasing member, the biasing member connecting the locking member and the second occlusion member, wherein the locking member may be secured to the tubular body with the biasing member biasing the second occlusion member against the external os of the cervix.

24. A method for providing an access lumen to a patient's uterus said method comprising:

introducing a tubular body through the cervical canal into the uterus;

expanding a first occlusion member over an exterior surface of the tubular body against the internal surface of the cervical os;

axially translating a second occlusion member relative to the first occlusion member to engage the second occlusion member against a surface of the external cervical os, wherein sufficient sealing force is provided to substantially inhibit loss of pressurized fluid from the uterus into the vagina; and directing a heated fluid through the tubular body and providing insulation to the tubular body to substantially inhibit heat from the fluid from transferring through the tubular body to the cervix, vagina, or surrounding tissue.

25. A method as in claim 24, wherein the first occlusion member is in a collapsed configuration which closely conforms the exterior surface when the tubular body is introduced through the cervical canal and is expanded to a conical configuration with a surface that engages the internal surface of the internal cervical os.

26. A method as in claim 25, wherein the first occlusion member comprises an evertible cylindrical surface which is expanded by axially compressing the cylindrical surface to cause the distal end to expand radially.

27. A method as in claim 26, wherein the evertible cylindrical surface comprises an elastomeric sheet covering a mesh.

28. A method as in claim 24, further comprising engaging a second occlusion member on the tubular body against a surface of the external cervical os to enhance anchoring and sealing.

29. A method as in claim 28, wherein the second occlusion member has a conical surface which is engaged against the surface of the external cervical os by axially translating the second occlusion member over the tubular body.

30. A method for providing an access lumen to a patient's uterus said method comprising:

introducing a tubular body through the cervical canal into the uterus;

expanding a first occlusion member over an exterior surface of the tubular body against the internal surface of the cervical os, wherein sufficient sealing force is provided to substantially inhibit loss of pressurized fluid from the uterus into the vagina; and directing a heated fluid through the tubular body and providing insulation to the tubular body to substantially inhibit heat from the fluid from transferring through the tubular body to the cervix, vagina, or surrounding tissue.

31. A method for providing an access lumen to a patient's uterus said method comprising:

introducing a tubular body through the cervical canal into the uterus;

expanding a first occlusion member over an exterior surface of the tubular body against the internal surface of the cervical os, wherein sufficient sealing force is provided to substantially inhibit loss of pressurized fluid from the uterus into the vagina;

wherein the first occlusion member is in a collapsed configuration which closely conforms the exterior surface when the tubular body is introduced through the cervical canal and is expanded to a conical configuration with a surface that engages the internal surface of the internal cervical os; and wherein the first occlusion member comprises an evertible cylindrical surface which is expanded by axially compressing the cylindrical surface to cause the distal end to expand radially.

32. A method for providing an access lumen to a patient's uterus said method comprising:

introducing a tubular body through the cervical canal into the uterus;

expanding a first occlusion member over an exterior surface of the tubular body against the internal surface of the cervical os;

axially translating a second occlusion member relative to the first occlusion member to engage the second occlusion member against a surface of the external cervical os, wherein sufficient sealing force is provided to substantially inhibit loss of pressurized fluid from the uterus into the vagina;

wherein the first occlusion member is in a collapsed configuration which closely conforms the exterior surface when the tubular body is introduced through the cervical canal and is expanded to a conical configuration with a surface that engages the internal surface of the internal cervical os; and wherein the first occlusion member comprises an evertible cylindrical surface which is expanded by axially compressing the cylindrical surface to cause the distal end to expand radially.

33. A method as in claim 32, further comprising directing a heated fluid through the tubular body and providing insulation to the tubular body to substantially inhibit heat from the fluid from transferring through the tubular body to the cervix, vagina, or surrounding tissue.

* * * * *